Figure 1:
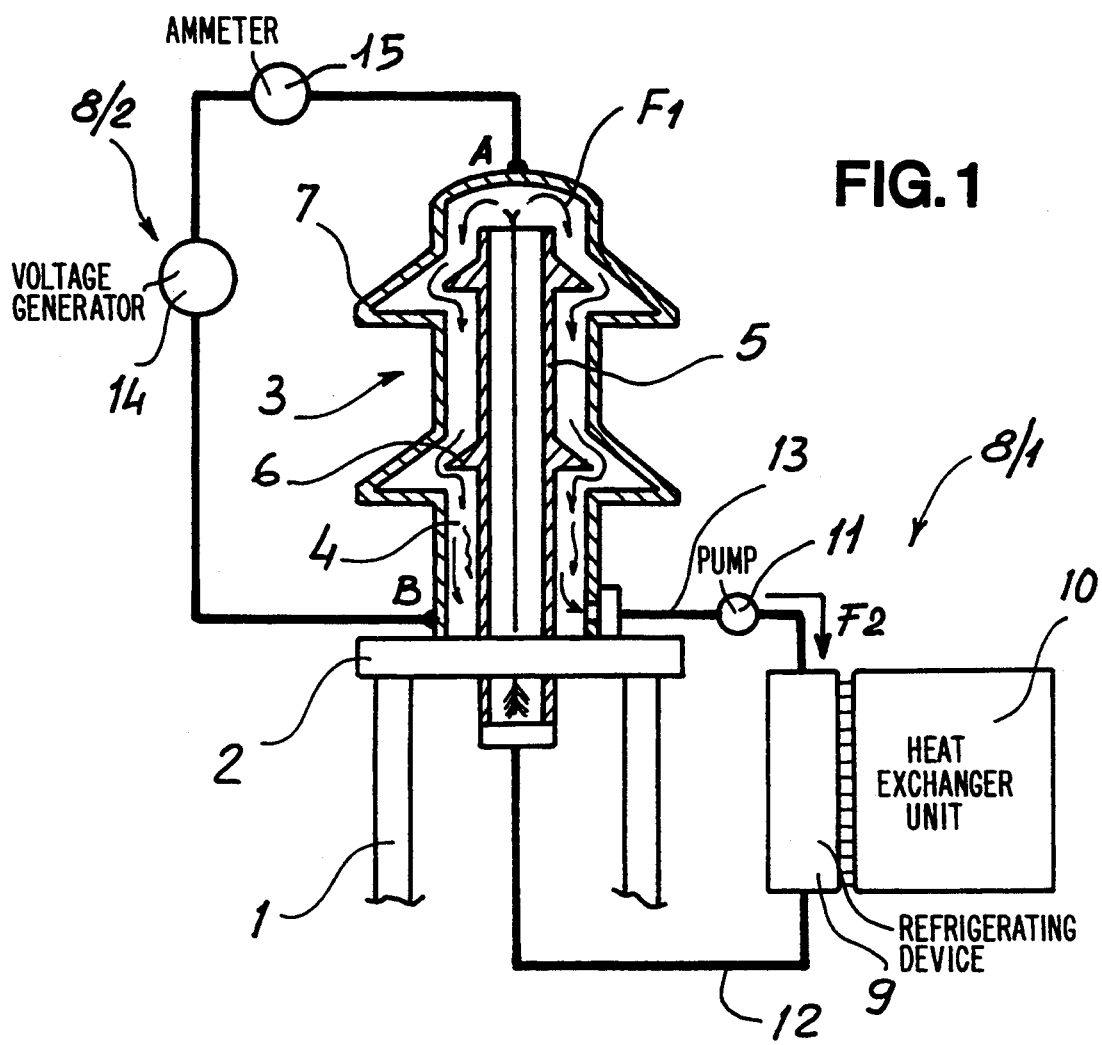

United States Patent [19]
Marrone

[11] Patent Number: 5,386,192
[45] Date of Patent: Jan. 31, 1995

[54] APPARATUS FOR CHECKING THE CONTAMINATION CONDITION OF ELECTRIC INSULATORS

[75] Inventor: Giovanni Marrone, Cologno Monzese, Italy

[73] Assignee: ENEL-Ente Nationale per l'Energia Elettrica, Cologno Monzese, Italy

[21] Appl. No.: 39,495

[22] PCT Filed: Sep. 7, 1992

[86] PCT No.: PCT/EP92/02062

§ 371 Date: Jun. 11, 1993

§ 102(e) Date: Jun. 11, 1993

[87] PCT Pub. No.: WO93/06471

PCT Pub. Date: Apr. 1, 1993

[30] Foreign Application Priority Data

Sep. 13, 1991 [IT] Italy ............... MI91 A 002435

[51] Int. Cl.[6] ................................ G01N 27/06
[52] U.S. Cl. ........................ 324/439; 324/552; 324/694; 324/722; 174/15.3; 174/11 BH
[58] Field of Search ............ 324/439, 525, 551, 552, 324/693, 694, 699, 700, 722, 71.2; 174/11 BH, 15.1, 15.3

[56] References Cited

U.S. PATENT DOCUMENTS

| | | | |
|---|---|---|---|
| 3,627,899 | 12/1971 | Moore | 174/15.3 |
| 3,807,489 | 4/1974 | Minbiole et al. | 174/15.1 X |
| 4,101,828 | 7/1978 | Dehler | 324/700 |
| 4,132,853 | 1/1979 | Wagenaar | 174/15.3 X |
| 4,169,965 | 10/1979 | Cronin | 174/15.3 |
| 4,237,415 | 12/1980 | Easley | 324/552 |
| 4,358,631 | 11/1982 | Matsuda | 174/15.3 |
| 5,136,856 | 8/1992 | Yamamoto et al. | 174/15.1 X |

Primary Examiner—Kenneth A. Wieder
Assistant Examiner—Glenn W. Brown
Attorney, Agent, or Firm—Keil & Weinkauf

[57] ABSTRACT

The apparatus comprises a probe-insulator (3) with an internal cavity, a first system (8/1) that circulates a cold fluid within the cavity (4) of the probe-insulator in order to cool the latter to such a temperature that the external humidity condenses on the external surface, a second system (8/2) for measuring the surface conductivity on the probe-insulator, a third system for activating a washing plant of all insulators installed in the same area when the measured value of said surface conductivity reaches a pre-set critical value; the refrigerating device that produces said cold fluid preferably includes a group of Peltier modules.

4 Claims, 2 Drawing Sheets

APPARATUS FOR CHECKING THE CONTAMINATION CONDITION OF ELECTRIC INSULATORS

The present invention relates to an apparatus for checking the contamination condition of electric insulators installed in the open in a given area, for instance the insulators of an electric station or sub-station.

In the following description, with insulators we intend those units made of porcelain, glass or other suitable insulating materials that afford the electrical insulation between two parts at different voltage of an open air electric plant.

A thorough checking of the contamination conditions of the external surfaces of such insulators allows the piloting of cleaning actions on the same insulators. It is noted that a drop in the insulating properties of an insulator also occurs when the contaminator deposit on its surface exceeds the critical threshold that depends on the shape and size of the insulator and on the voltage applied. This has led to the demand for an indicator of the quantity of contaminator deposit to be found on one insulator representative of a group of insulators installed within the same area and able to signal the moment in which said layer of deposit reaches the critical threshold and thus to activate the cleaning system action or, in absence of the latter, the start up of a cleaning action of the insulator group with voltage disconnected. In the description that follows we shall call "the probe-insulator" an insulator that is representative of the group of insulators in the same area, group that will normally be made up of insulators of different type and shape.

It appears that there are no such quantity indicators installed in Italy, but elsewhere there are apparatus that function as quantity indicators of the contaminator deposit. A first system is noted, comprising a probe-insulator exposed at a given height from the ground in the plant area and that is periodically lowered into an underlying tank so as to be washed in the water with the help of auxiliary means such as ultrasonic waves and the rotation around its axis of the insulator itself. All the contaminator materials deposited on the probe-insulator's surface gets washed into the water. At the end of each periodic wash the volume conductivity of the solution is measured, and this, naturally, tends to increase after each wash. In one instance comes the time when the measured value for conductivity is equal to the pre-set critical threshold. A second system is also noted that comprises a probe-insulator that, after being exposed, again at a certain height within the plant area, is periodically lowered and closed into a chamber in which steam, produced by a steam generator, humidifies the contaminator layer on the surface of the probe-insulator. Then the conductivity of this layer is measured and compared with the pre-set critical threshold.

A common disadvantage of both these systems consists in the mechanical complexity required for the automatic performance of the operative stages. For example, both the washing chambers and the humidifying chambers need devices for their opening and closing; especially the first must be kept closed and must open only for the time necessary to allow the entrance of the probe-insulator, and the systems must comprise mechanisms and control means for the movements of the probe-insulator relatively to the chambers. Another disadvantage of the first system relates to the fact that its use is limited to those cases in which the contaminator is easily soluble in water, as are generally marine pollutants. Another disadvantage pertaining to the second system is the need to adjust the steam generator in relation with the environmental conditions and the fact that this adjustment is made more complex and of uncertain result because the system works in the open; moreover, experience has proved the difficulty of completely humidifying the contaminator layer and, at the same time, avoiding that this layer be partly or totally washed away.

The invented apparatus obviates the aforementioned disadvantages and, as claimed, comprises: a probe-insulator featuring an internal cavity; a first system for the circulation within this internal cavity of a refrigerating fluid that will cool the probe-insulator to such a temperature that the outside humidity will condensate onto its external surface; a second system for measuring the surface conductivity of the probe-insulator cooled by said previous system; a third system for measuring the temperature and relative outside environment humidity, for activating said first and second systems proceeding to the survey, according to a pre-set sequence, of the probe-insulator's surface conductivity that has been cooled by the first system in order to reach a rating value for the conductivity, arresting the functions of said first system and said second system and compare the said rating value against a pre-set critical conductivity value producing an alarm signal as soon as said critical value is reached in order to activate a cleaning system for the insulators installed in the area or, in absence of the latter, the start up of a cleaning action of the same insulators with voltage disconnected.

The main advantages of the invented apparatus lie in the fact that one causes the humidifying of the contaminator deposit on the probe-insulator in a gradual and very close to natural process such as dew or fog that are the more frequent cause for insulator discharge; the duration of humidifying is accurately controllable and this avoids risks of washing out the surface of the probe-insulator during and after humidifying; the apparatus is highly reliable and simple in both its build-up and functioning.

Figure 2:
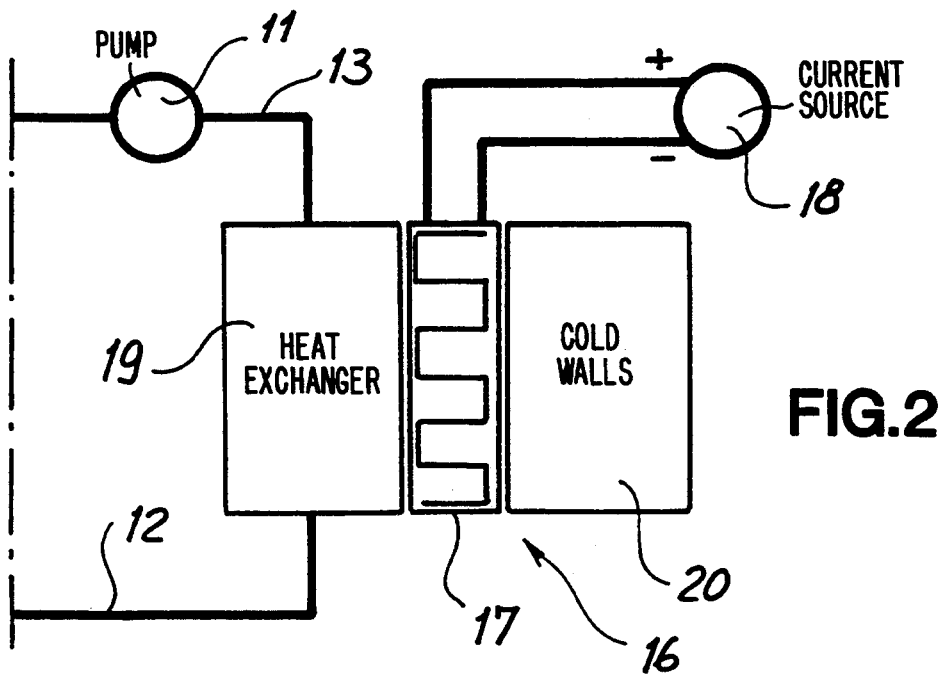

The above advantages and still others will become apparent in the following description of one of the ways of realizing the invention with reference to the attached drawings that show specific realizations in which FIG. 1 is an overall diagrammatic view of a first realization, FIG. 2 is a diagram of a second realization, and, FIG: 3 is a general diagram.

Figure 3:
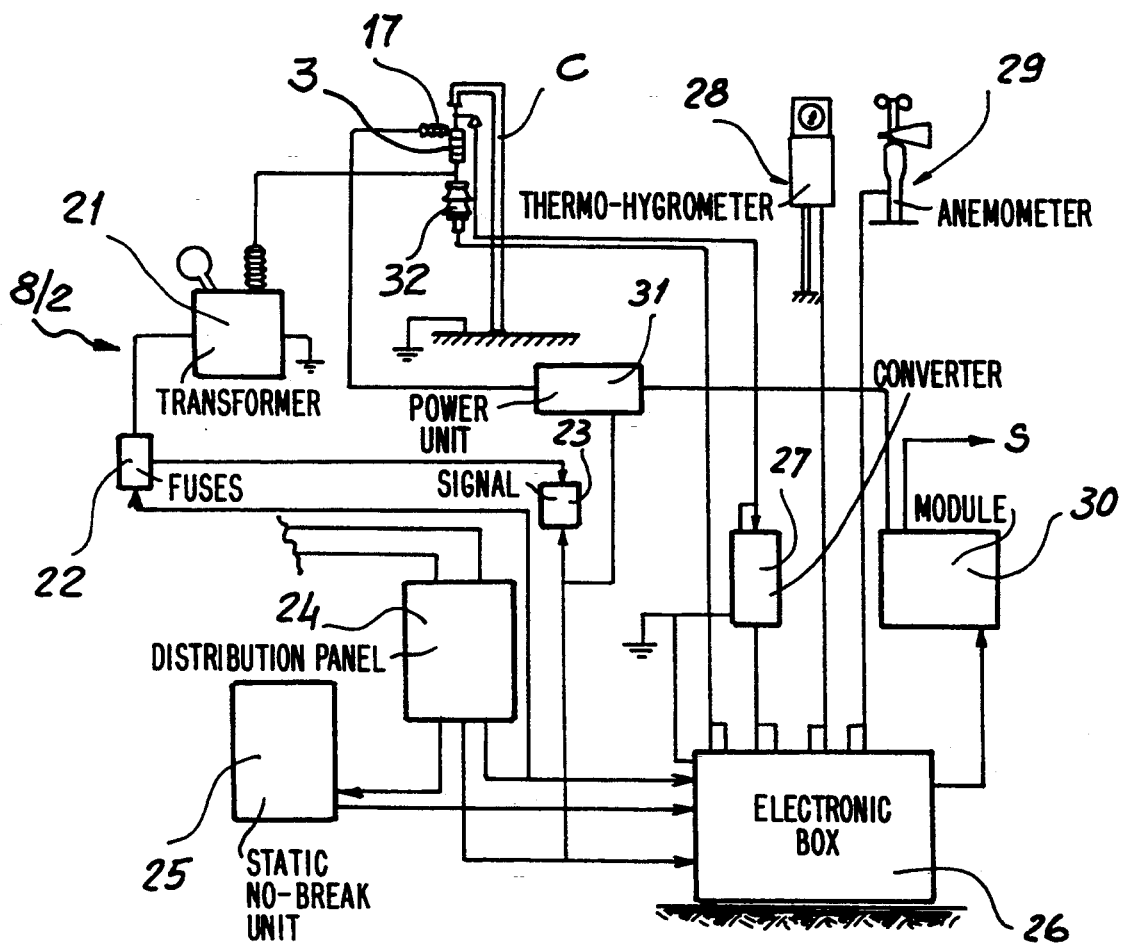

FIG. 1 shows: a) a support column 1 that carries an insulating shoe 2 at its top located at about 7 m. from the ground, within the yard of an electric substation; upon said shoe 2 a probe-insulator 3 is installed as defined above, with a pattern that is representative of the other insulators installed in the same area and that bears an internal cavity 4 with a profile that evidently follows the pattern of the outside profile (this probe-insulator 3 is 30 cms. high and has leak line of about 50 cms.); b) a tubular body of insulating material 5 with. projections 6, corresponding to the ribs 7 of the probe-insulator, is positioned within the latter through shoe 2; c) a first system 8/1 for the cooling comprising a conventional refrigerating device 9 (inverted Carnot cycle) the evaporator of which is associated with a heat exchanger within a unit 10; said first cooling system 8/1 gives a refrigerating fluid contained in the refrigerating device 9 a temperature of about 15° C. less than the temperature of the air surrounding said probe-insulator; by means of a pump 11, said system causes said refrigerated fluid to circulate in said internal cavity 4 through the inlet pipe 12 that enters the bottom side of the tubular body 5, follows the route shown by arrow F1 and ends up in the return pipe 13, according to arrow F2; d) a second system 8/2, shown in detail in the drawing FIG. 3, to measure the surface conductivity of the probe-insulator 3; in the figure only a voltage generator 14 for at least real 10 kV and an ammeter 15 fitted in an A-B circuit closed circuit between the top and the base of the probe-insulator 3 are shown.

FIG. 2 is the diagram of the refrigerating device of an apparatus that is perfectly similar to the one shown in FIG. 1, but in which the refrigerating device is realized with Peltier modules. As is known, according to the Peltier effect, at the contact surface between two conductors of different composition, passed through by continuous electricity heat is generated or absorbed, according to the direction of the current. Industry currently produces Peltier modules for diverse technical appliances and the device shown comprises a refrigerating system 16 that uses 20 Peltier modules 17, each made up by about 70 bismuth-tellurium thermo-couples, dimensions of the latter 29×22×5 mms., connected in parallel and fed by a continuous 12 V current from a source 18. Said pump 11 causes the refrigerated fluid to circulate within the cavity 4 of the probe-insulator 3 (not shown), through said pipes 12 and 13 and within the heat exchanger 19. One wall of said heat exchanger 19 is adjacent to the cold walls 20 of the 20 Peltier modules so that the fluid can be cooled to a temperature about 15° C. lower than that of environment temperature. The heat drawn from the fluid plus the thermal equivalent of the feed energy for the Peltier modules is dissipated in an exchanger 20.

FIG. 3 is a general diagram of an apparatus in which the refrigerating device is realized with 20 Peltier modules 17, as illustrated in FIG. 2. It is clear however, that with minor changes, this drawing also applies to an apparatus in which the refrigerating device is realized in a conventional manner, as shown in FIG. 1. The drawing is easily understandable so only the main parts are listed and the function of only some of these are explained. On an insulator 20, supported by a column C, a probe-insulator 3 is installed, identical to the one shown in FIG. 1 and associated to said unit of 20 Peltier modules 17, as previously described. The rest of the apparatus comprises: a transformer 21 that keeps the probe-insulator 3 at a voltage of 10 kV; fuses 22 protecting the feeding circuit of the transformer 21 and a signal 23 placed in a visible position to signal the possible burning out of said fuses; a sectioning and distribution panel 24 that is used to section the incoming electric lines to 220V/40A and 220V/6A that feed the static no-break unit 25 that supplies reserve power in case of network interruption and an electronic box 26 to control the apparatus; a box 27 to convert the measurement of the surface voltage into a digital signal; a thermo-hygrometer 28 to supply the values of relative outside environment temperature and humidity; an anemometer 29 to supply wind speed values; a module 30 to perform the comparison between the value measured and the memorised critical threshold and possibly start off an alarm signal; a unit 31 to provide continuous current power to the Peltier modules 17.

The embodiment shown in FIG. 2 adds other advantages to the ones mentioned above: the apparatus is very compact and the refrigerating system is totally static; faults in the refrigerating device are far less frequent and more easily repaired. Finally, the dia-thermal fluid used for refrigeration in Peltier modules is not a pollutant, differing as such from the conventional refrigerating fluids currently being accused for ecological reasons.

I claim:

1. An apparatus for checking the contamination conditions of electric insulators by measuring the quantity of contaminator material deposited on the external surface of a probe-insulator (3), which apparatus comprises: a probe-insulator (3) in a fixed position featuring an internal cavity (4); a first system (8/1) that circulates within the cavity (4) a cold fluid for cooling the probe-insulator (3) to a temperature such that the outside humidity condenses on the external surface of the probe-insulator; a second system (8/2) to measure the surface conductivity of the probe-insulator cooled by said first system (8/1); a third system that generates an alarm signal at the moment in which the surface conductivity measured on said cooled probe-insulator (3) reaches a pre-set critical conductivity value and hence activates an automatic washing plant for the insulators installed in that same area or commands a cleaning operation with insulators disconnected.

2. An apparatus according to claim 1 which comprises a system for measuring the outside environment relative temperature and humidity, to activate said first (8/1) and second (8/2) systems according to a pre-set sequence for the measurement of surface conductivity values on said cooled probe-insulator (3) until a measured value for said conductivity is obtained, to stop the action of said first (8/1) and second (8/2) systems and hence compare said measured value with the pre-set critical conductivity value and produce an alarm signal at the moment the measured value reaches the critical value so as to activate a washing plant for the insulators installed in that same area or command a washing operation with the same insulators disconnected.

3. An apparatus according to claim 1 characterized in that said first system (8/1) includes a conventional inverted Carnot cycle (9, 10) refrigerating device.

4. An apparatus according to claim 1 characterized in that said first system (8/1) includes a refrigerating device (16) that employs a number of Peltier modules (17).

* * * * *